(12) United States Patent
Rajgarhia

(10) Patent No.: US 6,733,800 B1
(45) Date of Patent: May 11, 2004

(54) SYNERGISTIC COMPOSITION FOR THE TREATMENT OF LIVER AND LIVER ASSOCIATED AILMENTS AND A PROCESS FOR PREPARING THE SAME

(76) Inventor: Ashok Rajgarhia, Rajgarhia Paper Mills Pvt. Ltd., 15, Exchange Place, Calcutta- 700 001 (IN)

(*) Notice: Subject to any disclaimer, the term of this patent is extended or adjusted under 35 U.S.C. 154(b) by 0 days.

(21) Appl. No.: 10/031,854

(22) PCT Filed: Oct. 14, 1999

(86) PCT No.: PCT/IN99/00055
§ 371 (c)(1),
(2), (4) Date: Jan. 24, 2002

(87) PCT Pub. No.: WO01/07062
PCT Pub. Date: Feb. 1, 2001

(30) Foreign Application Priority Data

Jul. 26, 1999 (IN) .................................................. 660/99
Jul. 26, 1999 (IN) .................................................. 661/99

(51) Int. Cl.[7] .............................................. A61K 35/78
(52) U.S. Cl. ........................................ 424/757; 424/725
(58) Field of Search ................................. 424/725, 757

(56) References Cited

U.S. PATENT DOCUMENTS 5,693,327 A * 12/1997 Shah

FOREIGN PATENT DOCUMENTS

| CN | 1096211 A | 12/1994 |
|---|---|---|
| CN | 1096211 | * 12/1994 |
| EP | 687465 | * 12/1995 |
| EP | 0687465 A1 | 12/1995 |
| EP | 0890360 A1 | 1/1999 |
| EP | 890360 | * 1/1999 |

OTHER PUBLICATIONS

Subramoniam et al. Indian J. Pharmacol. 1999. vol. 31, No. 3, pp. 166–175.*
Ram, V.J. Drug News Perspectives. 2001. vol. 14, No. 6, pp. 353–363.*

* cited by examiner

*Primary Examiner*—Christopher R. Tate
(74) *Attorney, Agent, or Firm*—Sidley Austin Brown & Wood LLP

(57) ABSTRACT

This invention relates to a synergistic composition for the treatment of liver and liver associated ailments and a process for preparing the same. The synergistic composition comprises the extract of Glycyrrhiza glabra and Picrorhiza kurroa in ratio 2-1:1-3 by weight. The process for preparing the composition comprises of the following steps: preparation of extract from the roots of Glycyrrhizia Glabra and Picrorhiza kurroa, optimization of the extract of Glycyrrhiza glabra to ensure the maximum content of glycyrrhizin, optimization of the extract of Picrorhiza kurroa to ensure maximum content of Kurkin, mixing the two extracts obtained in ratio 2-1:1-3 at ambient temperature and pressure to obtain the composition.

9 Claims, No Drawings

SYNERGISTIC COMPOSITION FOR THE TREATMENT OF LIVER AND LIVER ASSOCIATED AILMENTS AND A PROCESS FOR PREPARING THE SAME

The present invention relates to a synergistic composition for the treatment of liver and liver associated ailments and a process for preparing the same.

BACKGROUND

Liver is an important organ in the human body and is responsible for its well being. It helps in detoxifing any exogenous toxic substances present within the human body, which are consumed as drugs or with food. These toxic wastes reduce the efficiency of the liver as a blood purifier. Liver also undergoes frequent attacks by viral infections such as hepatitis.

India has the second largest pool of HBV carriers in the world. It has a population of over 45 million HBV carriers and 15 million HCV carriers. One fourth of these are at risk to suffer from chronic liver diseases and its lethal complications, such as cirrhosis or even liver carcinoma. Coupled with the burden of HBV related liver diseases, there is an ever increasing patient load due to Hepatitis C. Screening of all the blood before use for HIV, is still a distant reality and this contributes to a significant increase in chronic liver diseases in India.

Therefore it has become absolutely essential to develop an effective therapeutic strategy to tackle this problem.

In allopathy, at present no specific drug is available for providing adequate cover for protection of or preventing liver from various infections and diseases. In Ayurveda, many plant extracts are known, which have a hepatoprotective effect. However, the effect of such crude plant extracts as used in Ayurveda is slow by virtue of presence of other components which may prevent full action of the active ingredient/component.

One of the plant extracts used as medicine for treatment of liver diseases is the root extract of plant Glycyrrhiza glabra (liquorice).

Said extract contains flavonoids, saponins, oligoglycosides, phenolic compounds and glycyrrhizic acid. Glycyrrhiza glabra is known to have four actions which help in treatment and prevention of liver diseases (Sub acute liver failure, cirrhosis liver with activity)

Cyto-protective action—This helps in fortifying the cell, which enables the cell to protect itself from virus/infection.

Anti-inflammatory and Immunomodulatory action—This helps in reducing the inflammation of the organ and help modulate the organ to function normally. It also has cholerectic action.

Anti-oxidant action—Helps in preventing replication of virus.

Anti-viral action—The combined effect of the above helps in preventing replication of virus, thus there is reduction of viral load over a period of continued administration of the drug.

The activity of the extract of Glycyrrhiza glabra is also due to the action of beta glycyrrhizinic acid at the level of complement component C2.

However, liquorice extract when taken in large quantities for prolonged periods, causes high blood pressure ( hypertension), water retention, weight gain due to pseudoaldosteronism and possibly heart complications.

Extract of roots of Picorrhiza Kurroa have also been recommended as a hepatoprotective agent for protection of liver toxicity caused by hepatotoxic agents such as alcohol, carbon tetra chloride, viruses and parasites. Roots of Picrorrhiza kurroa contain glycosides, kutkin (kutkosides and picrosides) and other organic acids such as vallanic and cinnamic acids.

The extract of Picrorrhiza roots is bitter and it increases gastric secretion, diminishes the force of heartbeat and reduces the blood pressure.

Therefore there was a need to develop a synergistic composition having a pleasant flavour which would have hepatoprotective action, against the virus and at the same time enhance the protective action against hepatotoxic agents such as those in food, drug and alcohol.

The object of the present invention as therefore to provide for a synergistic composition having enhanced hepatoprotective action with reduced side effects.

Yet another object of the present invention is to provide for a composition having hepatoprotective effect against both viruses and hepatotoxic agents.

The aforesaid object is achieved by the present invention, which relates to a synergistic composition for the treatment of liver and liver associated ailments comprising:

extract of Glycyrrhiza glabra and Picrorhiza kurroa in ratio 2-1:1-3 by weight.

The said composition may be mixed with excipients for tableting.

The preset invention also provides a process for preparing a synergistic composition for the treatment of liver and liver associated ailments comprising:

preparation of extract from the roots of Glycyrrhizia Glabra and Picrorhiza kurroa, optimization of the extract of Glycyrrhiza glabra to ensure the maximum content of glycyrrhizin.

option of the extract of Picrorhiza kurroa to ensure maximum content of Kutkin.

mixing the two extracts obtained in ratio 2-1:1-3 at ambient temperature and pressure to obtain the composition.

The extract of Glycyrrhiza glabra is mixed with extract of Picrorhiza kurroa preferably in the ratio 1.25: 2.

The extracts of Glycyrrhiza glabra and Picrorhiza kurroa may be prepared in any known manner.

The extract of Glycyrrhiza Glabra may also be prepared after treating the powdered roots with a non polar solvent in the proportion of 1:5 by volume for removing unwanted components such as saponins, pigments and lipids in the supernatant. The residue obtained is mixed in 3–5 times volume of hot water at 60–90° C. and constantly stirred for 3–5 hours. This water mixture is acidified and the residue extracted and dried in such a way that optimum concentration of Glycyrrhizin is obtained. The extract is standardized on TLC plates to obtain a definite number of components in each batch of the extract.

The extract of Picrorhiza kurroa may also be obtained after treatment of the dried powdered roots of the plants with petroleum ether in the proportion 1:3 by volume. The residue extracted with alcohol (60%) and left in cold water to remove/reduce the content of undesired components and concentrated to dryness to get optimized extract of Picrorhiza kurroa. The extract can be standardized by TLC to get same constituents in each batch of extract.

The composition of the herbal extracts in the present drug will enhance the hepatoprotective activity and at the same time reduce harmful side effects.

Method of Optimization

Optimization of Liquorice Extract:

Glycyrrhizin content in liquorice root ranges from 3–6%. A standard curve is plotted of different UV readings taken from the after carrying out TLC test on of different conc. of pure Glycyrrhizin. The extract obtained from liquorice are put on TLC and the concentration of Glycyrrhizin in the extract is measured on UV and quantified with the help of the standard curve plotted above.

Optimization of Picrorhiza Kurroa Extract:

Similar procedure is carried out for optimizing the extract of Picrorhiza kurroa extract. Optimization is done to a stage of 40–70% content of Glycyrrhizin/Kutkin in the extracts.

The present invention will now be described with reference to foregoing examples:

EXAMPLE 1

The extract of Glycyrrhiza glabra is optimized at 50% Glycyrrhizin content. The extract of Picrorhiza kurroa is optimized at 40% kutkin content. 100 mg of Glycyrrhiza glabra extract is mixed with 20 mg of Picrorhiza Kurroa extract to prepare the composition. Excipients are added to make a tablet form.

EXAMPLE 2

The extract of Glycyrrhiza glabra is optimized at 60% Glycyrrhizin content. The extract of Picrorhiza kurroa is optimized at 40% kutkin content 84 mg of Glycyrrhiza glabra extract is mixed with 31.5 of Picrorhiza Kurroa extract to prepare the composition. Excipients are added to make a tablet form.

DOSAGE

Adult—2 Tablets Three times/day

Child—1 Tablet three times/day

I claim:

1. A synergistic composition for the treatment of liver and liver associated ailments consisting essentially of an extract of Glycyrrhiza glabra and an extract of Picrorhiza kurroa in a ratio of from 2-1:1-3 by weight.

2. A composition as claimed in claim 1 wherein the ratio of the extract of Glycyrrhiza glabra to that of the extract of Picrorhiza kurroa is 1.25:2.

3. The composition of claim 1 further consisting of an excipient.

4. A method for treating a human patient suffering from liver disease comprising administering to said patient an effective amount of a synergistic composition consisting essentially of extract of Glycyrrhiza glabra and extract of Picrorhiza kurroa in a ratio of from 2-1:1-3 by weight.

5. A method for treating a human patient suffering from ailments associated with liver disease comprising administering to said patient an effective amount of a synergistic composition consisting essentially of an extract of Glycyrrhiza glabra and an extract of Picrorhiza kurroa in a ratio of from 2-1:1-3 by weight.

6. The method of claim 4 wherein the ratio of the extract of Glycyrrhiza glabra to that of the extract of Picrorhiza kurroa is 1.25:2.

7. The method of claim 5 wherein the ratio of the extract of Glycyrrhiza glabra to that of the extract of Picrorhiza kurroa is 1.25:2.

8. The method of claim 4 wherein said synergistic composition further comprises an excipient.

9. The method of claim 5 wherein said synergistic composition further comprises an excipient.

* * * * *